United States Patent
Behling et al.

(10) Patent No.: US 12,080,508 B2
(45) Date of Patent: Sep. 3, 2024

(54) BALANCING X-RAY OUTPUT FOR DUAL ENERGY X-RAY IMAGING SYSTEMS

(71) Applicant: KONINKLIJKE PHILIPS N.V., Eindhoven (NL)

(72) Inventors: Rolf Karl Otto Behling, Norderstedt (DE); Steffen Holzapfel, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 307 days.

(21) Appl. No.: 17/628,615

(22) PCT Filed: Jul. 21, 2020

(86) PCT No.: PCT/EP2020/070591
§ 371 (c)(1),
(2) Date: Jan. 20, 2022

(87) PCT Pub. No.: WO2021/013853
PCT Pub. Date: Jan. 28, 2021

(65) Prior Publication Data
US 2022/0277919 A1   Sep. 1, 2022

(30) Foreign Application Priority Data
Jul. 22, 2019  (EP) ..................... 19187558

(51) Int. Cl.
*H01J 35/10* (2006.01)
*H01J 35/14* (2006.01)
*H01J 35/30* (2006.01)

(52) U.S. Cl.
CPC ............ *H01J 35/153* (2019.05); *H01J 35/10* (2013.01); *H01J 35/30* (2013.01); *H01J 2235/088* (2013.01)

(58) Field of Classification Search
CPC .......... H01J 35/153; H01J 35/10; H01J 35/30; H01J 2235/088
See application file for complete search history.

(56) References Cited

U.S. PATENT DOCUMENTS

| | | | | |
|---|---|---|---|---|
| 4,685,118 A | * | 8/1987 | Furbee | H05G 1/08 378/114 |
| 6,421,420 B1 | * | 7/2002 | Grodzins | H01J 35/153 378/113 |
| 2006/0104418 A1 | * | 5/2006 | Dunham | H01J 35/153 378/124 |
| 2008/0260101 A1 | | 10/2008 | Oreper | |
| 2012/0163530 A1 | | 6/2012 | Sainath | |

(Continued)

OTHER PUBLICATIONS

PCT International Search Report, International application No. PCT/EP2020/070591, Nov. 13, 2020.

*Primary Examiner* — Hugh Maupin
(74) *Attorney, Agent, or Firm* — Larry Liberchuk (57) ABSTRACT

An X-ray source (100) for generating X-ray radiation of first and second energy spectra is proposed, wherein the X-ray intensity imbalance between the first and second energy spectra is reduced as compared to conventional X-ray sources. The reduction of the X-ray intensity imbalance is achieved by configuring a smaller electron impact angle (141) onto the anode (102) when the higher tube voltage is applied as compared to when the lower tube voltage is applied.

11 Claims, 3 Drawing Sheets

(56) References Cited

U.S. PATENT DOCUMENTS

| | | |
|---|---|---|
| 2012/0269321 A1 | 10/2012 | Behling |
| 2013/0223594 A1* | 8/2013 | Sprong .................... H05G 1/30 378/140 |
| 2014/0105361 A1 | 4/2014 | Vogtmeier |
| 2015/0014526 A1 | 1/2015 | Bendahan |
| 2018/0096816 A1 | 4/2018 | Lemaitre |

* cited by examiner

BALANCING X-RAY OUTPUT FOR DUAL ENERGY X-RAY IMAGING SYSTEMS

FIELD OF THE INVENTION

The invention relates to an X-ray source for generating X-ray radiation of first and second energy spectra, an X-ray imaging system, a method for generating X-ray radiation, a computer program and a computer-readable medium.

BACKGROUND OF THE INVENTION

X-ray imaging systems are utilized in a number of applications such as medical diagnostics, airport security, material analysis and others. For example, in a computed tomography (CT) system, an X-ray source and an X-ray detector are arranged on opposite sides of a patient. The X-ray source may generate a fan beam of X-rays. The photons of the X-ray beam will be partially absorbed by the patient's body. Thereby, bones absorb more photons as compared to lean tissue. The photons passing through the patient's body are then received by the X-ray detector, which generates a shadow image of the patient's anatomy. The resulting image is a two-dimensional projection of the three-dimensional structure of the patient's body. In a CT system, the X-ray source and the X-ray detector rotate around the patient to capture images from different viewing directions. These images can be processed by a computer system to generate a three-dimensional image of the patient's anatomy.

The X-ray source typically comprises a cathode and an anode, which are arranged inside a vacuum tube. The cathode emits electrons, which are accelerated towards the anode due to a tube voltage supplied by a power supply. With a tube voltage of for example 80 kV, electrons are accelerated from the cathode to the anode reaching a kinetic energy of 80 keV when impinging onto the anode. This energy is converted fully or partially into X-ray radiation, which may radiate through an aperture in the housing of the X-ray tube.

The image quality provided by X-ray imaging systems can be improved by scanning the patient using X-ray radiation having multiple energy spectra. This allows imaging the patient with spectral material decomposition. This technique has proven to yield improved images while reducing the amount of toxic contrast dye, typically iodyne. X-ray radiation of different energy spectra can be generated by applying different tube voltages between the cathode and the anode of the X-ray tube. For example, tube voltages of 80 kV and 140 kV may be applied to generate softer and harder X-ray radiation, respectively.

SUMMARY OF THE INVENTION

It has been observed that the intensity of the X-ray radiation may be higher for the high tube voltage as compared to the low tube voltage. This imbalance of the X-ray intensity may be compensated, at least in part, at the X-ray detector of an X-ray imaging system by using longer integration periods for the low tube voltage as compared to the high tube voltage. However, in a CT system, the X-ray source and the X-ray detector typically rotate around the patient at a constant angular velocity so that the longer integration periods for the low tube voltage result in a reduced image resolution.

Hence, it may be desirable to provide an improved X-ray source for generating X-ray radiation of first and second energy spectra, wherein the imbalance of the X-ray intensity at different tube voltages is reduced.

This is achieved by the subject matter of the independent claims, wherein further embodiments are incorporated in the dependent claims and the following description. It should be noted that any feature, element, and/or function of the X-ray source, as described in the following, equally applies to the X-ray imaging system, the method for generating X-ray radiation, the computer program for controlling the X-ray source and the computer-readable medium, as described in the following, and vice versa.

According to the present disclosure, an X-ray source for generating X-ray radiation of first and second energy spectra is presented. The X-ray source comprises a cathode for emitting an electron beam, an anode for converting the electron beam at least partly into X-ray radiation, electron optics configured to control an impact angle at which electrons of the electron beam impinge onto the anode, a power supply configured to apply first and second tube voltages between the cathode and the anode, the second tube voltage being higher than the first tube voltage, and a control circuitry operably coupled to the electron optics, wherein the control circuitry is configured to control the electron optics such that the electrons of the electron beam impinge at a first mean impact angle onto the anode when the first tube voltage is applied and such that the electrons of the electron beam impinge at a second mean impact angle onto the anode when the second tube voltage is applied, and wherein the second mean impact angle is smaller than the first mean impact angle.

The impact angle is defined as the angle between the propagation path of the electron and the tangent plane to the surface of the anode at the location where the propagation path of the electron strikes the surface of the anode.

The X-ray radiation having the first energy spectrum may be generated by applying the first tube voltage between the cathode and the anode, whereas the X-ray radiation having the second energy spectrum may be generated by applying the second tube voltage between the cathode and the anode, the second tube voltage being higher than the first tube voltage. The power supply may generate first and second tube voltages of for example 80 kV and 140 kV, respectively. Due to the tube voltage, electrons emitted by the cathode are accelerated towards the anode. For example, with a tube voltage of 80 kV, electrons reach a kinetic energy of 80 keV before impinging onto the anode. At the anode, this energy may be converted partially or fully into X-ray radiation so that X-ray photons may have energies of up to 80 keV. In contrast, with the tube voltage of 140 keV, X-ray photons reach energies of up to 140 keV. The energy spectrum of the X-ray radiation may therefore comprise higher energies for the second tube voltage as compared to the first tube voltage.

Several types of cathodes may be used for the X-ray source of the present disclosure, including conventional thermionic cathodes, field emitter cathodes, Pierce-type cathodes, dispenser cathodes, photocathodes, or plasma cathodes. The anode of the X-ray source may comprise a material to generate X-ray radiation such as tungsten or molybdenum. The anode may be rotating so that the generation of heat in the focal spot, i.e., the surface section where the electrons impinge onto the anode, is spread over a larger area as compared to a stationary anode. However, the present invention is not limited to the case of a rotating anode.

The electrons of the electron beam from the cathode to the anode may impinge onto the anode from different impact angles. The impact angle takes values between 0° and 90°.

An impact angle of 90° corresponds to a propagation path of the electron that is orthogonal to the surface of the anode. The smaller the impact angle, the more grazing is the propagation path of the electron with respect to the surface of the anode.

The electron optics of the X-ray source are configured to control an impact angle at which electrons of the electron beam impinge onto the anode. The electron optics may comprise electrostatic and/or magnetic devices. For example, the electron optics may comprise one or more dipoles, one or more quadrupoles, etc. The electron optics may be configured to form the electron beam. In one scenario, the electron optics may be configured to form a narrow electron beam so that the impact angle of the electrons onto the anode is essentially the same for all electrons. In another scenario, the electron optics may be configured to form a broad electron beam so that the electrons impinge onto the anode from a wide range of impact angles. In another scenario, the electron optics may deflect the electron beam to change the mean impact angle of the electrons onto the anode without changing the width of the electron beam at the surface area of impact. In another scenario, the electron optics may be configured to deflect the electron beam and to also form the electron beam.

The control circuitry may comprise analog and/or digital components. For example, the control circuitry may comprise passive electronics such as resistors, capacitors or electronic filters, active electronics such as amplifiers or analog-to-digital converters, microcontrollers, microprocessors, memory units, etc. The control circuitry is operably coupled to the electron optics and configured to control the electron optics. In addition, the control circuitry may be operably coupled to the power supply and the control circuitry may be configured to control the power supply including the voltage generated by the power supply. Alternatively or additionally, the control circuitry may be configured to receive a signal indicative of the generated tube voltage from the power supply, and the control circuitry may be configured to control the electron optics based on the received signal from the power supply.

The power supply is configured to generate first and second tube voltages and to apply these voltages between the cathode and the anode. The power supply may be configured to switch frequently between these tube voltages. For example, in a CT system, the tube voltage may be switched frequently to reduce imaging artifacts due to movements of the patient (or the patient's internal organs) in the period between capturing low- and high-energy X-ray images from similar directions. The power supply may be configured to switch between the first and second tube voltages with a rate of 1 kHz, 2 kHz, 4 kHz or 10 kHz. The voltage generated by the power supply may also be switched at lower or higher rates. The cathode may not allow switching the tube current at such rates or its capacity to switch at such high rates may be intentionally reduced. With the X-ray tube of the present disclosure, the tube current may be held constant, either for the entire scan time or at least for the periods when the tube voltage changes, notably during ramping the tube voltage down. The tube current may be substantially the same in periods when the first and second tube voltages are applied. Since the second tube voltage is higher than the first tube voltage, the electrical power of the electron beam may be higher for the second tube voltage as compared to the first tube voltage.

For tube voltages used for medical imaging, a major part of the electrical power of the electron beam is converted into heat, and the higher electrical power of the electron beam with the second tube voltage may exceed the thermal capacity of the anode. However, according to the present disclosure, the control circuitry is configured to control the electron optics such that the electrons of the electron beam impinge at a second mean impact angle onto the anode when the second tube voltage is applied, the second mean impact angle being smaller than the first mean impact angle of the electrons configured when the first tube voltage is applied. By configuring smaller impact angles for the second tube voltage, the electron back-scattering rate may be increased, resulting in a smaller fraction of the electrical power of the electron beam being converted into heat. The smaller impact angles of the electrons for the second tube voltage may therefore facilitate higher electrical powers of the electron beam. This may be utilized to apply high tube currents without exceeding the power limit of the anode when the second tube voltage is applied.

The conversion efficiency, that means, the fraction of the electrical power of the electron beam that is converted into X-ray radiation may be higher for the second tube voltage as compared to the first tube voltage when similar impact angles were configured for these voltages. Furthermore, the fraction of the X-ray radiation absorbed by an object such as a patient's body in a medical X-ray imaging system may be higher for the first tube voltage as compared to the second tube voltage. Thus, assuming that similar impact angles and similar tube currents were configured for the first and second tube voltages, the X-ray intensity at the X-ray detector of an X-ray imaging system may be significantly higher for the second tube voltage as compared to the first tube voltage.

As explained above, the imbalance of the X-ray intensity may be compensated, at least in part, by using longer integration periods at the X-ray detector of an X-ray imaging system for the first tube voltage as compared to the second tube voltage. However, in a CT system, the X-ray source and the X-ray detector typically rotate around the patient at a constant angular velocity so that the longer integration periods for the first tube voltage result in a reduced image resolution.

Alternatively, the imbalance of the X-ray intensity may be mitigated by controlling the tube current emitted by the cathode such that the tube current is higher when the first tube voltage is applied as compared to when the second tube voltage is applied. However, as explained above, it may be desired to switch the tube voltage frequently, and the tube current control may be too slow to compensate the X-ray intensity imbalance, in particular when the tube voltage is switched between each integration period. For example, conventional thermionic cathodes may allow switching the tube current at a rate of 10 Hz, whereas the tube voltage may be switched with a rate of 10 kHz.

Alternatively, to increase the X-ray intensity at the first tube voltage, the tube current emitted by the cathode may be increased. However, when the same high tube current is applied at the first and second tube voltages, the power limit of the anode may be exceeded in periods when the second tube voltage is applied, resulting a reduced lifetime of the X-ray source.

According to the present disclosure, the imbalance of the X-ray intensity may be reduced by configuring smaller impact angles for the second tube voltage compared to the first tube voltage. The conversion efficiency may be smaller for small electron impact angles as compared to large electron impact angles, so a smaller fraction of the electrical power of the electron beam may be converted into X-ray radiation for small electron impact angles. The smaller electron impact angles onto the anode for the second tube voltage may therefore result in a reduced X-ray intensity at the X-ray detector, so that the X-ray intensity imbalance between the first and second tube voltages may be reduced.

In an example, the second mean impact angle at which electrons of the electron beam impinge onto the anode is less than 70°.

The conversion efficiency for the second tube voltage may be reduced and the X-ray intensity imbalance between the first and second tube voltages may be mitigated by configuring smaller impact angles of the electrons onto the anode for the second tube voltage compared to the first tube voltage. The first mean impact angle for the first tube voltage may be close to 90°, that means the propagation paths of the electrons may be essentially orthogonal to the surface of the anode when the first tube voltage is applied. To achieve a significant reduction of the conversion efficiency for the second tube voltage, the second mean impact angle of the electrons may be decreased to less than 70°. Hence, when the second tube voltage is applied, the second mean impact angle of less than 70° may result in a significantly reduced conversion efficiency as compared to a second mean impact angle of 90°, which may directly translate into a reduced X-ray intensity at the X-ray detector of an X-ray imaging system. In other examples, the second mean impact angle at which the electrons impinge onto the anode may be less than 60°, 50°, 40°, 30° or 20°.

In another example, the electrons of the electron beam impinge onto a first surface section of the anode when the first tube voltage is applied and onto a second surface section of the anode when the second tube voltage is applied, wherein the first surface section overlaps with the second surface section.

The X-ray source may be applied in an X-ray imaging system. Differences between the first and second surface sections of the anode may result in imaging artifacts so that X-ray images captured for the first and second X-ray energy spectra may become more difficult to compare or to combine. Therefore, it may in principle be desired to have identical first and second surface sections of the anode, i.e., to have first and second surface sections of approximately the same size and at approximately the same location relative to the interface of the X-ray source with the X-ray system. Typically, this means that the areas of electron impact onto the anode, the first and second surface sections of the anode, basically coincide. The first and section surface sections of the anode are considered to have approximately the same size when their sizes differ by not more than 20%. Hence, the control circuitry may be configured to control the electron optics such that the size of the first surface section differs from the size of the second surface section by, for example, less than 20% or less than 10%. Alternatively or additionally, the control circuitry may be configured to control the electron optics such that a parameter indicating the size of the first surface section (for example a diameter of the first surface section in a certain direction) differs from the corresponding parameter indicating the size of the second surface section by, for example, less than 20% or less than 10%. In other examples, it may be desirable that the second surface section is larger than the first surface section and/or that the second surface section overlaps with the first surface section. Then, the first and second surface sections may together span a larger section of the surface of the anode as compared to identical first and second surface sections. Thus, the section of the surface of the anode where heat is generated due to the impinging electrons may be larger as compared to an example with identical first and second surface sections. This spread of the generation of heat over a larger surface section of the anode may allow increasing the electrical power of the electron beam without exceeding the power limit of the anode.

In another example, the center of the first surface section coincides with the center of the second surface section of the anode.

The center of the first surface section may be defined, for example, as the average location on the surface of the anode where electrons impinge when the first tube voltage is applied. Alternatively, the center of the first surface section may be defined as, for example, the location on the surface of the anode where the likelihood that electrons impinge at this location is maximum when the first tube voltage is applied. The center of the second surface section is preferably defined similarly to the center of the first surface section. Hence, the center of the second surface section may be defined as the average location on the surface of the anode where electrons impinge when the second tube voltage is applied. Alternatively, the center of the second surface section may be defined as the location on the surface of the anode where the likelihood that electrons impinge at this location is maximum when the second tube voltage is applied.

Here and in the following, the center of the first surface section is said to coincide with the center of the second surface section when the two centers differ by in an amount that is negligible as compared to the size of the smaller of the first and second surface sections. In particular, the control circuitry may be configured to control the electron optics such that the center of the first surface section differs from the center of the second surface section by less than 20%, or, preferably, less than 10%, relative to the diameter of the smaller of the first and second surface sections in the direction of the difference between the centers of the first and second surface sections.

In another example, the electron optics comprise a first deflection device and a second deflection device, wherein the first deflection device is switchable between a first state and a second state, wherein the control circuitry is configured to switch the first deflection device from the first state to the second state in accordance with switching the power supply from the first tube voltage to the second tube voltage, and wherein the first and second deflection devices provide a deflection of the electron beam when the first deflection device is in the second state.

The first and second deflection devices may each comprise one or more magnetic devices and/or one or more electrostatic devices, including dipoles, quadrupoles, etc.

The control circuitry may be configured to control the first deflection device such that the first deflection device deflects the electron beam when the second tube voltage is applied and such that the first deflection device does not deflect the electron beam when the first tube voltage is applied. Alternatively, the control circuitry may be configured to control the first deflection device such that the first deflection device provides a stronger deflection of the electron beam when the second tube voltage is applied as compared to when the first tube voltage is applied. The control circuitry may configure the first state when the first tube voltage is applied by the power supply, whereas the second state may be configured when the second tube voltage is applied.

The second deflection device may be configured to steer the electron beam, which may have been deflected by the first deflection device, onto a first surface section of the anode when the first tube voltage is applied and onto a second surface section of the anode when the second tube voltage is applied, wherein the first and second surface sections of the anode may overlap, or wherein the first and second surface sections of the anode may have coinciding centers, or wherein the first and second surface sections of the anode may be identical. The second deflection device may also be switchable and the control circuitry may be configured to control the second deflection device.

The deflection of the electron beam in the second state is provided so that the second mean impact angle is smaller than the first mean impact angle. The electrons of the electron beam may be deflected by the first deflection device in a direction radial to a rotational axis of the anode. Additionally or alternatively, the electrons of the electron beam may be deflected by the first deflection device in a direction that is orthogonal to both the radial direction and the axis of rotation of a rotating anode or the normal to the anode target of a stationary anode.

In another example, the electron optics comprise a focusing device and a defocusing device, wherein the electron optics are switchable between a third state and a fourth state, wherein the control circuitry is configured to switch the electron optics from the third state to the fourth state in accordance with switching the power supply from the first tube voltage to the second tube voltage, and wherein, in the fourth state, the defocusing device first provides a broadening of the electron beam, and the focusing device subsequently provides a focusing of the broadened electron beam.

The focusing and defocusing devices may each comprise one or more magnetic devices and/or one or more electrostatic devices, including dipoles, quadrupoles, etc.

The control circuitry may be configured to control the defocusing device such that the defocusing device increases the width of the electron beam when the second tube voltage is applied and such that the defocusing device does not broaden the electron beam when the first tube voltage is applied. Alternatively, the control circuitry may be configured to control the defocusing device such that the defocusing device provides a stronger broadening of the electron beam when the second tube voltage is applied as compared to when the first tube voltage is applied.

Furthermore, the control circuitry may be configured to control the focusing system such that the focusing system focuses the electron beam, which may have been broadened by the defocusing device, onto a first surface section of the anode when the first tube voltage is applied and onto a second surface section of the anode when the second tube voltage is applied, wherein the first and second surface sections of the anode may have comparable or identical sizes as outlined above, and/or wherein the first and second surface sections may overlap, and/or wherein the center of the first surface section of the anode may coincide with the center of the second surface section of the anode.

The control circuitry may configure the third state when the first tube voltage is supplied by the power supply, whereas the fourth state may be configured when the second tube voltage is supplied. The broadening and, subsequently, the focusing of the electron beam in the fourth state are provided to reduce the second mean impact angle. For example, the center direction of the electron beam may be orthogonal to the surface of the anode. However, with a broad electron beam, electrons may also impinge onto the surface of the anode at impact angles that are significantly smaller than 90°. Consequently, with a broad electron beam, the mean impact angle of the electrons may be significantly smaller than 90°, even if the center direction of the electron beam may be orthogonal to the surface of the anode.

The electron beam may be broadened in a direction radial to a rotational axis of a rotating anode or the normal of the anode target for a stationary anode. Additionally or alternatively, the electron beam may be broadened in a direction that is orthogonal to both the axis of rotation or the normal of the anode target for a stationary anode and the corresponding radial direction.

In another example, the electron optics comprise a first deflection device, a second deflection device, a focusing device and a defocusing device, wherein the electron optics are switchable between a fifth state and a sixth state, wherein the control circuitry is configured to switch the electron optics from the fifth state to the sixth state in accordance with switching the power supply from the first tube voltage to the second tube voltage, and wherein, in the sixth state, the first and second deflection devices provide a deflection of the electron beam and the focusing and defocusing devices provide a broadening and, subsequently, a focusing of the electron beam.

In another example, the defocusing device provides a stronger broadening of the electron beam when the electron optics are in the fourth state as compared to the third state.

The center direction of the electron beam may be orthogonal or almost orthogonal to the surface of the anode. Then, the broadening of the electron beam by the defocusing device and the subsequent focusing of the broadened electron beam onto a surface section of the anode may result in a reduced mean impact angle as compared to a configuration, in which the electron beam is not broadened.

In another example, the anode comprises a substrate, which is at least partially coated with first and second coating layers, the first coating layer being arranged between the second coating layer and the substrate, wherein the substrate comprises a first material to generate X-ray radiation, wherein the first coating layer comprises a second material, which is transparent for X-ray radiation and the electrons of the electron beam, wherein the second coating layer comprises a third material to generate X-ray radiation, and wherein an X-ray filter is attached to the second coating layer to filter X-ray radiation generated in the second coating layer.

The electron beam may first impinge onto the second coating layer. The electrical power of the electron beam may be converted partially into X-ray radiation when the electron beam impinges onto the second coating layer. The mean impact angle of the electrons onto the second surface section of the anode is smaller when the power supply generates the second tube voltage as compared to when the first tube voltage is supplied.

Due to the smaller mean impact angle of the electrons for the second tube voltage, the propagation path through the second coating layer may on average be longer for the second tube voltage than for the first tube voltage. The fraction of electrons that propagate through the second coating layer may therefore be smaller for the second tube voltage as compared to the first tube voltage. Hence, the fraction of the electrons that impinge onto the substrate may be smaller for the second tube voltage as compared to the first tube voltage. For this reason, the fraction of the X-ray radiation that is generated in the second coating layer relative to the sum of the X-ray radiation that is generated in the second coating layer and the substrate may be higher for the second tube voltage as compared to the first tube voltage. In other words, when the second tube voltage is applied, then most of the X-ray radiation may be generated in the second coating layer, and only a rather small fraction of the X-ray radiation may be generated in the substrate, whereas, when the first tube voltage is supplied, then a major fraction of the X-ray radiation may be generated in the substrate.

The X-ray filter may be arranged such that the X-ray filter filters X-ray radiation generated in the second coating layer, and such that the X-ray filter does not filter the X-ray radiation generated in the substrate. To accomplish this, the first coating layer may provide a sufficient gap between the substrate and the second coating layer, so that the X-ray filter is arranged sufficiently apart from the substrate.

The X-ray filter may comprise a material such as molybdenum and the filtering of the X-ray radiation generated in the second coating layer may result in an increase of a measure for a difference between the first energy spectrum of the X-ray radiation generated when the first tube voltage is applied and the second energy spectrum of the X-ray radiation generated when the second tube voltage is applied. For example, the X-ray filter may increase the difference between the mean photon energies of the first and second energy spectra. Providing X-ray radiation with more different first and second energy spectra may allow capturing more meaningful X-ray images in a dual energy X-ray imaging system.

Furthermore, the X-ray filter may filter a larger fraction of the X-ray radiation when the second tube voltage is applied as compared to when the first tube voltage is applied. The filtering of the X-ray radiation results in a reduction of the X-ray intensity. Hence, the X-ray filter may cause a stronger reduction of the X-ray intensity for the second tube voltage as compared to when the first tube voltage is applied. This may result in a reduction of the X-ray intensity imbalance at the X-ray detector of an X-ray imaging system.

The first material of the substrate may be rhenium. The second material of the first coating layer may be diamond or a carbon-based fiber-reinforced composite. The third material of the second coating layer may be tungsten. The X-ray filter may comprise molybdenum or another filtering material, which has no k-edge in the portion of the X-ray spectrum relevant for X-ray imaging. These materials may comprise aluminum, titanium, tin, or iron or a combination thereof.

In another example, the second coating layer has a thickness of less than 1 micrometer at a surface section where the electrons of the electron beam impinge onto the second coating layer.

The thickness of the second coating layer may generally be determined such that the difference between a first fraction of X-ray radiation and a second fraction of X-ray radiation is large or maximum, wherein the first fraction of X-ray radiation is the fraction of X-ray radiation generated in the second coating layer relative to the sum of the X-ray radiation generated in both the second coating layer and the substrate when the first tube voltage is applied. Similarly, the second fraction of X-ray radiation may be the fraction of X-ray radiation generated in the second coating layer relative to the sum of the X-ray radiation generated in both the second coating layer and the substrate when the second tube voltage is applied. The second coating layer may have a thickness of 1 μm. However, thinner or thicker second coating layers are also possible, depending on the composition of the second coating layer, the composition of the substrate, the first and second tube voltages, and the electron impact angles.

According to the present disclosure, also an X-ray imaging system is presented. The X-ray imaging system comprises an X-ray source according to any one of the preceding claims and an X-ray detector, wherein the X-ray detector is arranged to receive X-ray radiation emitted by the X-ray source.

The X-ray imaging system may be applied for example for medical imaging or airport security systems. When the X-ray source generates X-ray radiation of the first energy spectrum, the X-ray detector may capture first image data of an object. Similarly, when the X-ray source generates X-ray radiation of the second energy spectrum, the X-ray detector may capture second image data. The first and second energy spectra may be different, so that the first image data may provide different information about an object than the second image data. The first and second image data may be displayed separately, or the first and second image data may be processed separately, for example to detect structures or materials, or the first and second image data may be combined to render an image based on both the first and second image data.

In an example, the X-ray imaging system further comprises a detector control circuitry, wherein the detector control circuitry controls the X-ray detector to generate first image data when the first tube voltage is applied between the cathode and the anode of the X-ray source and to generate second image data when the second tube voltage is applied. Thereby, an integration period for generating the first image data may have the same duration as compared to an integration period for generating the second image data.

The X-ray source of the present disclosure may provide X-ray radiation with a reduced intensity imbalance for first and second tube voltages as compared to conventional X-ray sources. This may be achieved by configuring a smaller impact mean impact angle for the second tube voltage as compared to the first tube voltage. The reduced X-ray intensity imbalance for the first and second tube voltages may allow to use more similar X-ray detector integration periods when the first and second tube voltages are applied. In particular, a first X-ray detector integration period may be used when the first tube voltage is applied, and a second X-ray detector integration period may be used when the second tube voltage is applied, wherein the first and second integration periods may have the same or similar durations.

According to the present disclosure, also a method for generating X-ray radiation of first and second energy spectra using an X-ray source comprising a cathode for emitting an electron beam, an anode for converting the electron beam at least partly into X-ray radiation, a power supply for applying a tube voltage between the cathode and the anode, electron optics configured to control an impact angle at which electrons of the electron beam impinge onto the anode, and a control circuitry operably coupled to the electron optics is presented. Generating X-ray radiation of the first energy spectrum comprises the following steps, not necessarily in this order: (i) applying, by the power supply, a first tube voltage, and (ii) controlling, by the control circuitry, the electron optics such that the electrons of the electron beam impinge at a first mean impact angle onto the anode.

Further, generating X-ray radiation of the second energy spectrum comprises the following steps, not necessarily in this order: (i) applying, by the power supply, a second tube voltage, wherein the second tube voltage is higher than the first tube voltage, and (ii) controlling, by the control circuitry, the electron optics such that the electrons of the electron beam impinge at a second mean impact angle onto the anode, wherein the second mean impact angle is smaller than the first mean impact angle.

According to the present disclosure, also a computer program is presented, wherein the computer program comprises instructions for causing the X-ray source as defined in the independent claims to carry out the steps of the method for generating X-ray radiation of first and second energy spectra.

According to the present disclosure, also a computer-readable medium is presented, wherein the computer-readable medium stores the computer program of the present disclosure.

It shall be understood that the X-ray source, the X-ray imaging system, the method for generating X-ray radiation, the computer program for controlling the X-ray source and the computer-readable medium having stored such computer program according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
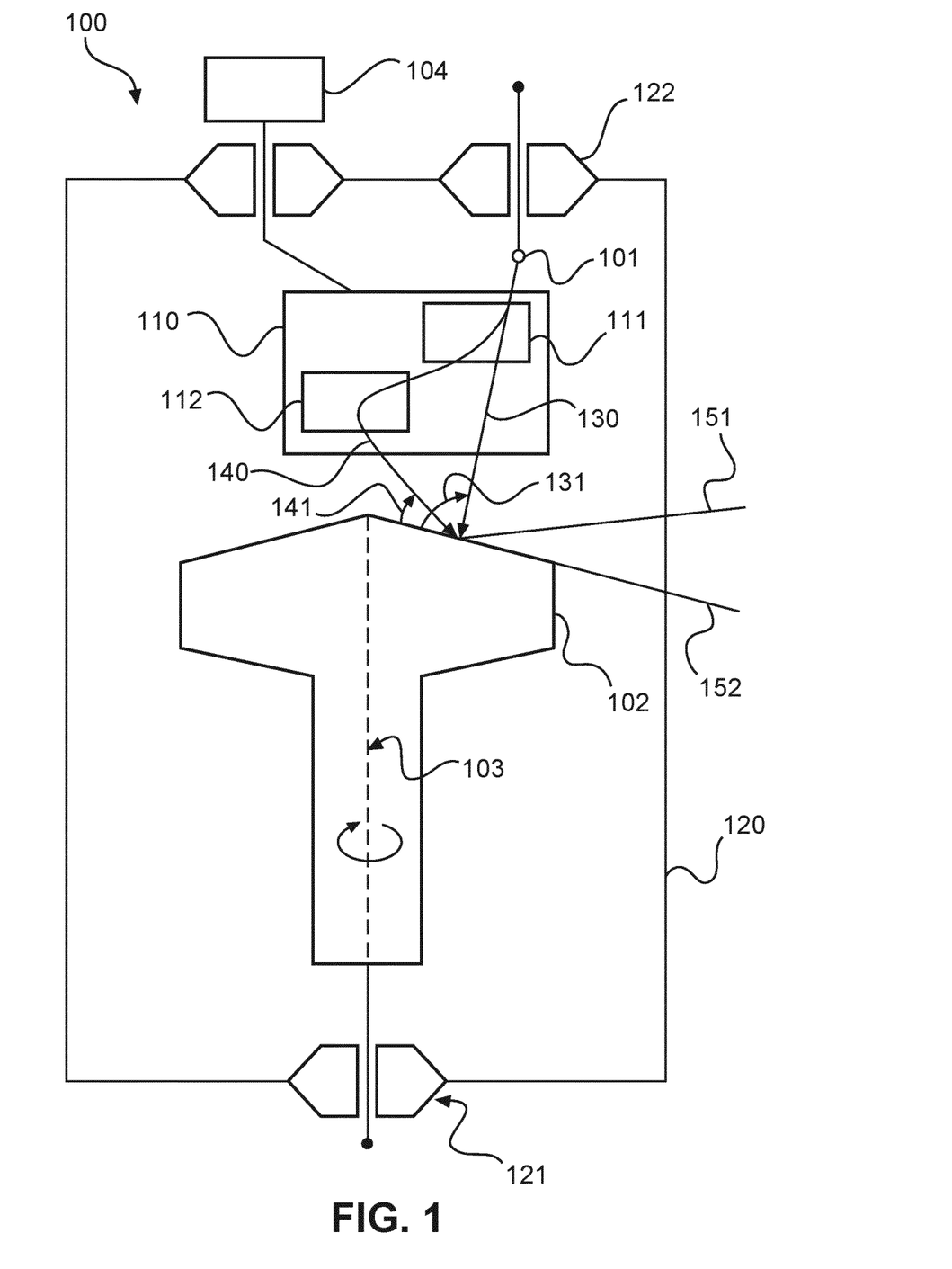
FIG. 1 shows schematically and exemplarily a first embodiment of an X-ray source for generating X-ray radiation of first and second energy spectra.

FIG. 1 shows schematically and exemplarily a first embodiment of an X-ray source 100 for generating X-ray radiation of first and second energy spectra. The X-ray source comprises a cathode 101 and an anode 102. The cathode and the anode are arranged inside a tube 120, which is preferably a vacuum tube. The anode may be rotating around the axis 103, but this is not necessary for the present disclosure.

A cathode insulator 122 and an anode insulator 121 allow to electrically contact the cathode and the anode, respectively, so that a tube voltage can be applied between the cathode and the anode by means of a power supply (not shown in the figure). The power supply may be configured to supply first and second tube voltages, wherein the second tube voltage is higher than the first tube voltage. For example, the power supply may be configured to supply a first tube voltage of 80 kV and a second tube voltage of 140 kV. Due to the tube voltage, electrons emitted by the cathode may be accelerated towards the anode. For example, when the first tube voltage of 80 kV is applied between the cathode and the anode, electrons may reach a kinetic energy of 80 keV before impinging onto the anode. This energy is partially or fully converted into X-ray radiation when the electrons impinge onto the anode. Hence, the X-ray photons may have energies up to 80 keV when the first tube voltage is applied, and up to 140 keV when the second tube voltage is applied. By applying different tube voltages, it is therefore possible to generate X-ray radiation having different energy spectra. The power supply may also be configured to generate more than two voltages, which may be utilized to generate X-ray radiation of more than two energy spectra. The X-rays 151 and 152 illustrate the emission of X-ray radiation through an aperture in the tube 120.

FIG. 1 also shows electron optics 110. The electron optics are operably connected to the control circuitry 104, the control circuitry being configured to control the electron optics. In FIG. 1, the control circuitry is arranged outside the tube 120, but the control circuitry may alternatively be arranged inside the tube. In FIG. 1, the electron optics 110 comprise a first deflection device 111 and a second deflection device 112. The control circuitry 104 may be configured to control the first deflection device such that electrons propagate along the path 130 from the cathode towards the anode when the first tube voltage is applied and such that electrons propagate along the path 140 when the second tube voltage is applied. Thereto, the control circuitry may be configured to control the first deflection device such that the first deflection device provides a deflection of the electron beam when the second tube voltage is supplied, whereas the first deflection device may provide a weaker or no deflection of the electron beam when the first tube voltage is supplied. When the electrons propagate from the cathode to the anode along the path 130, the second deflection device 112 may have a negligible impact on the electron path, whereas the second deflection device significantly changes the direction of the electron path when the electrons propagate from the cathode towards the anode along the path 140. In FIG. 1, narrow electron beams are assumed, i.e., the electrons propagate along approximately the same path 130 when the first tube voltage applied and along approximately the same path 140 when the second tube voltage is applied.

FIG. 1 also illustrates that the electrons impinge onto the anode at a small impact angle 141 when the second tube voltage is supplied, whereas the electrons impinge onto the anode at a large impact angle 131 when the first tube voltage is supplied. Thus, the control circuitry 104 controls the electron optics 110 such that electrons impinge at a first impact angle 131 onto the anode when the first tube voltage is applied and such that the electrons impinge at a smaller second impact angle 141 onto the anode when the second tube voltage is applied.

A major part of the electrical power of the electron beam may be converted into heat. The tube current may be the same for the first and second voltages, so the electrical energy of the electron beam may be higher for the second tube voltage as compared to the first tube voltage. The higher electrical power of the electron beam with the second tube voltage may exceed the power limit of the anode when the electrons would impinge with an impact angle close to 90° onto the anode. However, due to the reduced impact angle 141 when the second tube voltage is applied, the electron back-scattering rate is increased, resulting in a smaller fraction of the electrical power of the electron beam being converted into heat. The smaller impact angles of the electrons for the second tube voltage may therefore facilitate higher electrical powers of the electron beam. This may be utilized to apply a high tube current without exceeding the power limit of the anode when the second tube voltage is applied.

Assuming the same electron impact angles for first and second tube voltages, the conversion efficiency, that means, the fraction of the electrical power of the electron beam that is converted into X-ray radiation may be higher for the second tube voltage as compared to the first tube voltage. Furthermore, the fraction of the X-ray radiation absorbed by an object such as a patient's body in a medical X-ray imaging system may be smaller for the second tube voltage as compared to the first tube voltage. As a result, the X-ray intensity at the X-ray detector of an X-ray imaging system may be significantly higher for the second tube voltage as compared to the first tube voltage when similar impact angles were configured for these voltages.

However, according to the present disclosure, smaller impact angles are configured for the second tube voltage as compared to the first tube voltage. The conversion efficiency may be smaller for small electron impact angles as compared to large electron impact angles, so a smaller fraction of the electrical power of the electron beam may be converted into X-ray radiation for small electron impact angles. The smaller electron impact angles for the second tube voltage may therefore result in a reduced X-ray intensity at the X-ray detector, so that the X-ray intensity imbalance between the first and second tube voltages may be reduced.

Figure 2:
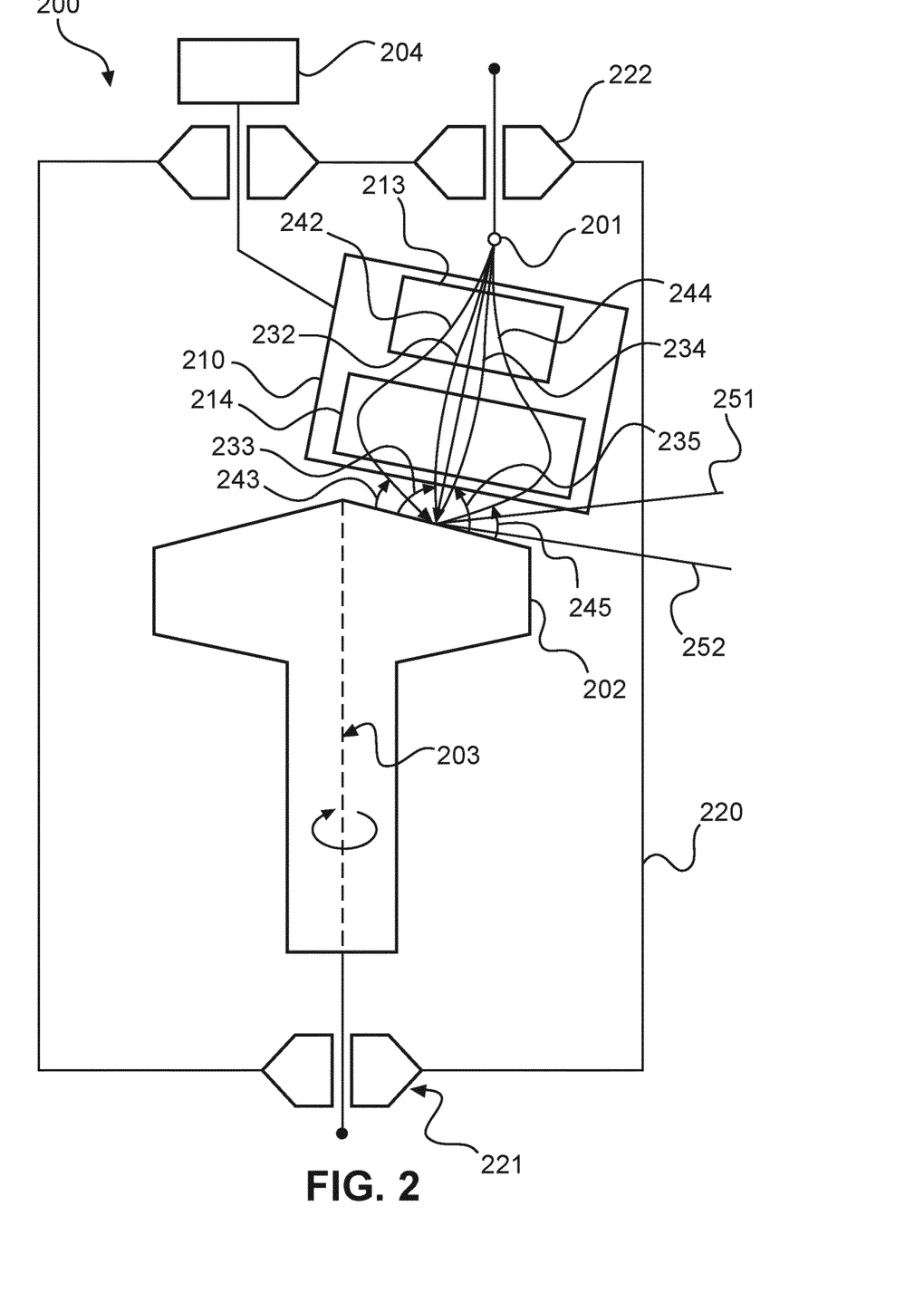
FIG. 2 shows schematically and exemplarily a second embodiment of an X-ray source for generating X-ray radiation of first and second energy spectra.

FIG. 2 shows schematically and exemplarily a second embodiment of an X-ray source 200 for generating X-ray radiation of first and second energy spectra. The X-ray source comprises a cathode 201 and an anode 202. The cathode and the anode are arranged inside a tube 220, preferably a vacuum tube. The anode is preferably rotating around the axis 203, but the invention is applicable also in the case of a stationary anode.

A cathode insulator 222 and an anode insulator 221 allow to electrically contact the cathode and the anode, respectively, so that a tube voltage can be applied between the cathode and the anode by means of a power supply (not shown in the figure). The power supply may be configured to supply first and second tube voltages, wherein the second tube voltage is higher than the first tube voltage. Due to the tube voltage, electrons emitted by the cathode are accelerated towards the anode. When impinging onto the anode, the kinetic energy of the electrons may be partially or fully converted into X-ray radiation. By applying different tube voltages, X-ray radiation of different energy spectra may be generated. The power supply may also be configured to supply more than two tube voltages, which may be utilized to generate X-ray radiation of more than two energy spectra. The X-rays 251 and 252 illustrate the emission of X-ray radiation through an aperture in the tube 220.

FIG. 2 also shows electron optics 210. The electron optics are operably connected to the control circuitry 204, the control circuitry being configured to control the electron optics. In FIG. 2, the control circuitry is arranged outside the tube 220, but the control circuitry may alternatively be arranged inside the tube. The electron optics 210 comprise a defocusing device 213 and a focusing device 214. The control circuitry 204 may be configured to control the electron optics 210 such that the defocusing device 213 provides a weak or no defocusing of the electron beam from the cathode to the anode when the first tube voltage is applied and a strong defocusing of the electron beam when the second tube voltage is applied. Furthermore, the control circuitry may be configured to control the focusing device 214 such that the electrons are focused on a first surface section of the anode when the first tube voltage is applied and onto a second surface section of the anode when the second tube voltage is applied, wherein the first and second surface sections of the anode are identical. Alternatively (not illustrated by the figure), the control circuitry may be configured to control the focusing device 214 such that the first and second surface sections overlap, or such that the first surface section lies within the second surface section, or such that the first and second surface sections have coinciding centers as outlined above. Hence, when the first tube voltage is applied between the cathode and the anode, the electron beam may be limited by the propagation paths 232 and 234, whereas the electron beam may be limited by the propagation paths 242 and 244 when the second tube voltage is applied. In other words, the electron optics form a narrow electron beam when the first tube voltage is applied and a broad electron beam when the second tube voltage is applied. FIG. 2 also depicts the minimum impact angles 233 and 235 when the first tube voltage is applied. The minimum impact angles 233 and 235 are equal to each other when the central direction of the electron beam is orthogonal to the surface of the anode and when the electron beam is symmetrical with respect to this central direction. Similarly, when the second tube voltage is applied, the minimum impact angles are 243 and 245. Clearly, the minimum impact angles 243 and 245 are smaller than the minimum impact angles 233 and 235, i.e., the impact angles of the electrons onto the anode are spread over a larger range of angles when the second tube voltage is applied as compared to when the first tube voltage is applied. Consequently, the mean impact angle may be smaller when the second tube voltage is applied as compared to when the first tube voltage is applied.

Due to the reduced mean impact angle when the second tube voltage is applied, the electron back-scattering rate is increased and the conversion efficiency is reduced. This may result in a reduction of the X-ray intensity imbalance for low and high tube voltages as explained above.

Figure 3:
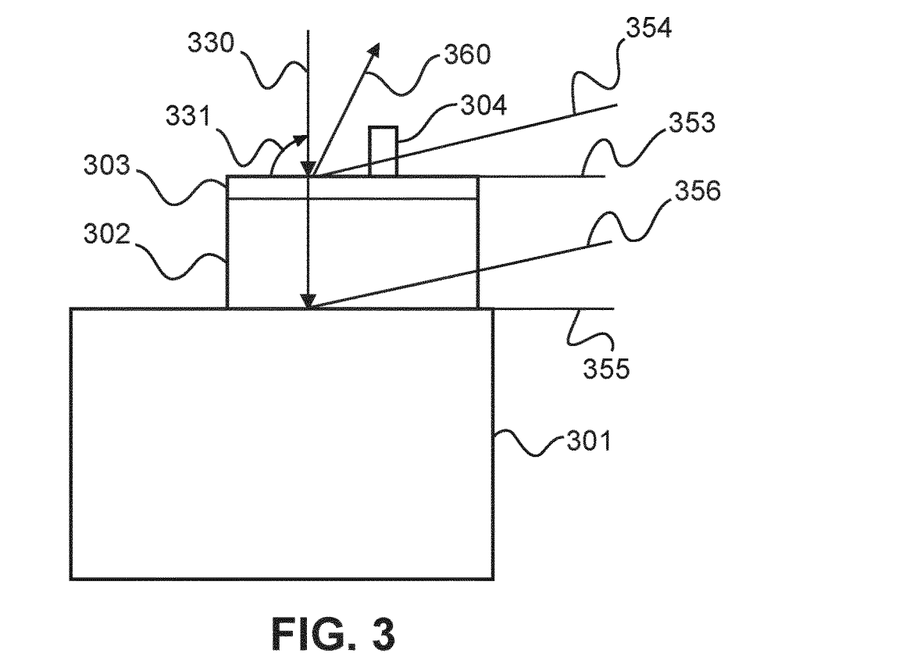
FIG. 3 shows schematically and exemplarily a part of an anode for an X-ray source with an electron beam impinging onto the anode from a large impact angle.

FIG. 3 shows schematically and exemplarily a part of an anode for an X-ray source. The anode comprises a substrate 301, which is at least partially coated with a first coating layer 302 and a second coating layer 303. An electron beam 330 impinges onto the second coating layer of the anode from an impact angle 331 equal to 90°. The second coating layer comprises a material to generate X-ray radiation such as tungsten. Hence, the energy of impinging electrons may be partially or fully converted into X-ray radiation. The X-rays 353 and 354 illustrate a cone of X-rays that radiate from the second coating layer through an aperture in the tube of the X-ray source (the tube not being shown in the figure). An X-ray filter 304 is attached to the second coating layer 303 to filter X-ray radiation generated in the second coating layer. A fraction of the impinging electrons may be backscattered, which is illustrated by the electron ray 360. Another fraction of the impinging electrons propagates through the second coating layer and through the first coating layer, wherein the first coating layer preferably comprises a material that is transparent for electrons. Thus, a fraction of the electrons impinges onto the substrate, which comprises a material to generate X-ray radiation such as rhenium. Hence, a fraction of the electrons impinges onto the substrate, where the energy of the electrons may be partially or fully converted into X-ray radiation. The X-rays 355 and 356 illustrate a cone of X-rays generated in the substrate, wherein the X-rays radiate through the aperture in the X-ray tube (not shown in the figure).

Figure 4:
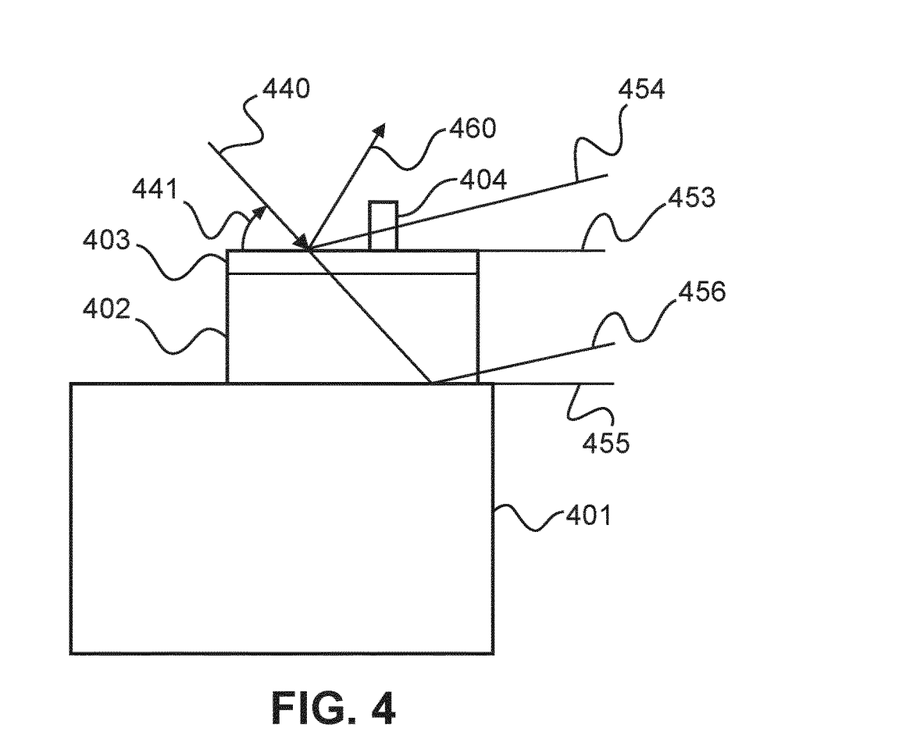
FIG. 4 shows the part of the anode of FIG. 3 with an electron beam impinging onto the anode from a small impact angle.

FIG. 4 shows schematically and exemplarily the part of the anode that is also shown in FIG. 3. Again, the anode comprises a substrate 401, which is at least partially coated with a first coating layer 402 and a second coating layer 403. An electron beam 440 impinges onto the second coating layer of the anode from an impact angle 441. The second coating layer comprises a material to generate X-ray radiation such as tungsten. Hence, the energy of impinging electrons may be partially or fully converted into X-ray radiation. The X-rays 453 and 454 illustrate a cone of X-rays that radiate from the second coating layer through an aperture in the X-ray tube (the tube not being shown in the figure). An X-ray filter 404 is attached to the second coating layer 403 to filter X-ray radiation generated in the second coating layer. A fraction of the impinging electrons may be backscattered, which is illustrated by the electron ray 460. Another fraction of the impinging electrons propagates through the second coating layer and through the first coating layer, wherein the first coating layer preferably comprises a material that is transparent for electrons. Thus, a fraction of the electrons impinges onto the substrate, which comprises a material to generate X-ray radiation such as rhenium. Hence, a fraction of the electrons impinges onto the substrate, where the energy of the electrons may be partially or fully converted into X-ray radiation. The X-rays 455 and 456 illustrate a cone of X-rays generated in the substrate, wherein the X-rays radiate through the aperture in the X-ray tube (not shown in the figure).

In FIG. 4, the electrons impinge onto the anode from a smaller impact angle 441 as compared to the impact angle 331 in FIG. 3. Due to the smaller impact angle, the electron back-scattering rate may be larger in FIG. 4 as compared to FIG. 3. The small impact angle of FIG. 4 may be configured when the second (high) tube voltage is applied between the cathode and the anode of an X-ray source, whereas the large impact angle of FIG. 3 may be configured when the first (low) tube voltage is applied. Assuming a constant tube current, the electrical power of the electron beam is larger for the second tube voltage as compared to the first tube voltage, and the smaller impact angle may facilitate a larger electrical power of the electron beam when the second tube voltage is applied without exceeding the power limit of the anode.

Furthermore, due to the smaller impact angle in FIG. 4, the propagation path through the second coating layer may be longer as compared to FIG. 3. The fraction of electrons that propagate through the second coating layer may therefore be smaller in FIG. 4 as compared to FIG. 3. Hence, the fraction of the electrons that impinge onto the substrate may be smaller in the case of FIG. 4 as compared to FIG. 3. For this reason, the fraction of the X-ray radiation that is generated in the second coating layer relative to the sum of the X-ray radiation that is generated in the second coating layer and the substrate may be higher for FIG. 4 as compared to FIG. 3. In other words, in FIG. 4, most of the X-ray radiation may be generated in the second coating layer, and only a rather small fraction of the X-ray radiation may be generated in the substrate, whereas, in the case of FIG. 3, a major fraction of the X-ray radiation may be generated in the substrate. Since the X-ray filter is arranged to filter the X-ray radiation generated in the second coating layer, the X-ray filter may be more effective when the electron impact angle is small as compared to when the electron impact angle is large. As noted before, the small impact angle of FIG. 4 may be configured when the second (high) tube voltage is applied between the cathode and the anode of an X-ray source, whereas the large impact angle of FIG. 3 may be configured when the first (low) tube voltage is applied. Hence, the X-ray filter may be more effective when the second tube voltage is applied as compared to when the first tube voltage is applied. The X-ray filter may comprise a material such as molybdenum and the filtering of the X-ray radiation generated in the second coating layer may result in an increase of a measure for a difference between the first energy spectrum of the X-ray radiation generated when the first tube voltage is applied and the second energy spectrum of the X-ray radiation generated when the second tube voltage is applied. For example, the X-ray filter may increase the difference between the mean photon energies of the first and second energy spectra. Providing X-ray radiation with more different first and second energy spectra may allow capturing more meaningful X-ray images in a dual energy X-ray imaging system.

Assuming again that the second tube voltage is applied in the scenarios depicted of FIG. 4 and that the first tube voltage is applied in the scenario of FIG. 3, the X-ray filter may filter a larger fraction of the X-ray radiation when the second tube voltage is applied as compared to when the first tube voltage is applied. The filtering of the X-ray radiation results in a reduction of the X-ray intensity. Hence, the X-ray filter may cause a stronger percent reduction of the X-ray intensity when the second tube voltage is applied as compared to when the first tube voltage is applied. This may result in a reduction of the X-ray intensity imbalance at the X-ray detector of an X-ray imaging system.

The second coating layer may have a thickness of less than 1 micrometer. The thickness of the second coating layer may generally be determined such that the difference between a first fraction of X-ray radiation and a second fraction of X-ray radiation is large or maximum, wherein the first fraction of X-ray radiation is the fraction of X-ray radiation generated in the second coating layer relative to the sum of the X-ray radiation generated in both the second coating layer and the substrate when the first tube voltage is applied. Similarly, the second fraction of X-ray radiation may be the fraction of X-ray radiation generated in the second coating layer relative to the sum of the X-ray radiation generated in both the second coating layer and the substrate when the second tube voltage is applied. The thickness of the second coating layer may be chosen depending on the material of the second coating layer, the material of the substrate, the first and second tube voltages and the electron impact angles.

It has to be noted that embodiments of the invention are described with reference to different subject matters. However, a person skilled in the art will gather that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray source for generating X-ray radiation of first and second energy spectra, the X-ray source comprising:
a cathode for emitting an electron beam;
an anode for converting the electron beam at least partly into X-ray radiation;
electron optics configured to control an impact angle at which electrons of the electron beam impinge onto the anode;
a power supply configured to apply first and second tube voltages between the cathode and the anode, the second tube voltage being higher than the first tube voltage; and
a control circuitry operably coupled to the electron optics;
wherein the control circuitry is configured to control the electron optics such that the electrons of the electron beam impinge at a first mean impact angle onto the anode when the first tube voltage is applied and such that the electrons of the electron beam impinge at a second mean impact angle onto the anode when the second tube voltage is applied; and
wherein the second mean impact angle is smaller than the first mean impact angle;
wherein the electron optics comprise a first deflection device and a second deflection device, wherein the first deflection device is switchable between a first state and a second state;
wherein the control circuitry is configured to switch the first deflection device from the first state to the second state in accordance with switching the power supply from the first tube voltage to the second tube voltage; and
wherein the first and second deflection devices provide a deflection of the electron beam when the first deflection device is in the second state.

2. The X-ray source according to claim 1, wherein the second mean impact angle at which electrons of the electron beam impinge onto the anode is less than 70 degrees.

3. The X-ray source according to claim 1,
wherein the electrons of the electron beam impinge onto a first surface section of the anode when the first tube voltage is applied and onto a second surface section of the anode when the second tube voltage is applied; and
wherein the first surface section overlaps with the second surface section.

4. The X-ray source according to claim 3, wherein a center of the first surface section coincides with a center of the second surface section of the anode.

5. The X-ray source according to claim 1,
wherein the electron optics comprise a focusing device and a defocusing device, the electron optics being switchable between a third state and a fourth state;
wherein the control circuitry is configured to switch the electron optics from the third state to the fourth state in accordance with switching the power supply from the first tube voltage to the second tube voltage; and
wherein in the fourth state, the defocusing device provides a broadening of the electron beam and subsequently provides a focusing of the broadened electron beam.

6. The X-ray source according to claim 5, wherein the defocusing device provides a stronger broadening of the electron beam when the electron optics are in the fourth state compared to the third state.

7. The X-ray source according to claim 1,
wherein the anode comprises a substrate, which is at least partially coated with first and second coating layers, the first coating layer being arranged between the second coating layer and the substrate;
wherein the substrate comprises a first material to generate the X-ray radiation;
wherein the first coating layer comprises a second material, which is transparent for the X-ray radiation and the electrons of the electron beam;
wherein the second coating layer comprises a third material to generate the X-ray radiation; and
wherein an X-ray filter is attached to the second coating layer to filter the X-ray radiation generated in the second coating layer.

8. The X-ray source according to claim 7,
wherein the first material of the substrate is rhenium;
wherein the second material of the first coating layer is diamond;
wherein the third material of the second coating layer is tungsten; and
wherein the X-ray filter comprises molybdenum.

9. The X-ray source according to claim 7, wherein the second coating layer has a thickness of less than 1 micrometer at a surface section where the electrons of the electron beam impinge onto the second coating layer.

10. A method for generating X-ray radiation of first and second energy spectra, comprising:
emitting an electron beam by a cathode of an X-ray source;
converting the electron beam at least partly into X-ray radiation, wherein a power supply is configured to apply a tube voltage between the cathode and an anode of the X-ray source;
controlling, by electron optics, an impact angle at which electrons of the electron beam impinge onto the anode;
applying a first tube voltage;
controlling the electron beam to impinge at a first mean impact angle onto the anode;
applying a second tube voltage, wherein the second tube voltage is higher than the first tube voltage; and
controlling the electron beam to impinge at a second mean impact angle onto the anode, wherein the second mean impact angle is smaller than the first mean impact angle;
wherein the electron optics comprise a first deflection device and a second deflection device, wherein the first deflection device is switchable between a first state and a second state;
wherein the first deflection device is switchable from the first state to the second state in accordance with switching the first tube voltage to the second tube voltage; and
wherein the first and second deflection devices provide a deflection of the electron beam when the first deflection device is in the second state.

11. A non-transitory computer-readable medium having executable instructions stored thereon which, when executed by at least one processor, cause the at least one processor to perform a method for generating X-ray radiation of first and second energy spectra, the method comprising:
emitting an electron beam by a cathode of an X-ray source;
converting the electron beam at least partly into X-ray radiation, wherein a power supply is configured to apply a tube voltage between the cathode and an anode of the X-ray source;
controlling an impact angle at which electrons of the electron beam impinge onto the anode;
applying a first tube voltage;

controlling the electron beam to impinge at a first mean impact angle onto the anode;
applying a second tube voltage, wherein the second tube voltage is higher than the first tube voltage; and
controlling the electron beam to impinge at a second mean impact angle onto the anode, wherein the second mean impact angle is smaller than the first mean impact angle;
wherein the electron optics comprise a first deflection device and a second deflection device, wherein the first deflection device is switchable between a first state and a second state;
wherein the first deflection device is switchable from the first state to the second state in accordance with switching the first tube voltage to the second tube voltage; and
wherein the first and second deflection devices provide a deflection of the electron beam when the first deflection device is in the second state.

\* \* \* \* \*